US008822200B2

United States Patent
Wang

(10) Patent No.: US 8,822,200 B2
(45) Date of Patent: Sep. 2, 2014

(54) METHOD FOR OPEN DIATOM CULTIVATION

(75) Inventor: Zhaokai Wang, Guangdong (CN)

(73) Assignee: Shenzhen Jawkai Bioengineering R & D Center Co., Ltd., Shenzhen, Guangdong (CN)

( * ) Notice: Subject to any disclaimer, the term of this patent is extended or adjusted under 35 U.S.C. 154(b) by 0 days.

(21) Appl. No.: 13/882,296

(22) PCT Filed: Jul. 13, 2011

(86) PCT No.: PCT/CN2011/077113
§ 371 (c)(1),
(2), (4) Date: Apr. 29, 2013

(87) PCT Pub. No.: WO2012/028040
PCT Pub. Date: Mar. 8, 2012

(65) Prior Publication Data
US 2013/0210122 A1    Aug. 15, 2013

(30) Foreign Application Priority Data

Nov. 3, 2010    (CN) .......................... 2010 1 0531486

(51) Int. Cl.
*C12N 1/12* (2006.01)
*A01G 33/00* (2006.01)

(52) U.S. Cl.
CPC .. *C12N 1/12* (2013.01); *A01G 33/00* (2013.01)
USPC .......................................... 435/257.1; 47/1.4

(58) Field of Classification Search
None
See application file for complete search history.

(56) References Cited

FOREIGN PATENT DOCUMENTS

CN           1710060 A  * 12/2005  ............... C12N 1/12

OTHER PUBLICATIONS

English translation of Weifa, Zheng Bao et al. Triangular brown algae open culture method and its special culture medium. 2005. Chinese Patent Application Publication No. CN 1710060 A. pp. 1-9 plus original images.*

* cited by examiner

*Primary Examiner* — John S. Brusca
*Assistant Examiner* — Sharon M Papciak
(74) *Attorney, Agent, or Firm* — Jackson IPG PLLC

(57) ABSTRACT

Provided is an open diatom cultivation method where continuous production of one or more selected diatom species achieve dominancy in the production system and that dominancy is maintained. The algae culture solution containing diatoms is first introduced to an open microalgae culture system. Then, carbon dioxide and nutrient salts are added to form a culture solution for diatom cultivation. The method enables industrial scale cultivation of diatoms at economically competitive production cost, with a high cultivation density and for a high production volume. The method also enables continuous stable production of selected diatoms and solves the difficult problem of controlling invading algae by always using the most competitive of local diatoms without imposing a selected algae which may be superior in some localities and under some climate conditions.

6 Claims, No Drawings

METHOD FOR OPEN DIATOM CULTIVATION

TECHNICAL FIELD OF THE INVENTION

The invention relates to microalgae culture techniques, particularly to a method for diatom cultivation, and more particularly to a method for diatom cultivation in an open reactor.

BACKGROUND OF THE INVENTION

Diatom, a type of microalgae, is the main food for fishes, shellfish and shrimps, especially for their larvae, and creates primary productivity in ocean together with other plants. In terms of biological taxonomy, diatom resides in Bacillariophyta, and based on shell shape and pattern arrangement mode, diatoms can be classified into two classes: centric diatoms (Centrales), which are radially symmetrical and pennate diatoms (Pennales), which are bilaterally symmetrical. The former are paraphyletic to the latter. CN200310120738.3 discloses a diatom culture solution and a method for diatom culture by the culture solution. In closed culture, the culture solution need to be measured frequently and quantitatively supplemented. High-density monoculture of diatoms requires complex production process and high cost.

Existing microalgae culture methods can be classified in two types: close culture and open culture. In open culture microalgae cultivation is performed using an open bioreactor such as runway pond, round shallow pond culture device and other culture devices, and it is featured by low investment; currently, only a few algae, like spirulina, chlorella and dunaliella, have been produced in industrial production by the open cultivation technique, whereas continuous open diatom cultivation has not been done in large scale, because the difficulty in the maintenance of a selected species in open culture due to the invasion of other species and predators Closed photo-bioreactors have been used for microalgae cultivation, such as air-lift culture device, stirring culture device and tube culture device; the closed culture can be used for producing high-value products (e.g. medicines or healthcare products) or used as a seed tank for open pond culture, where the high cost of closed production system is less important.

SUMMARY OF THE INVENTION

The invention provides an economically competitive method of large scale open diatom cultivation.

The technical proposal adopted by the invention for achieving the inventive objective is that: a method for open diatom cultivation, in which an open microalgae culture device is used, algae culture solution containing diatoms is introduced to the open microalgae culture, and then carbon dioxide and nutrient salts are added to maintain a culture solution for diatom cultivation. When required to control the invasion of predators the pH value of the algae culture solution is controlled to be between 3.0 and 5.0 and maintained so for 30 to 120 minutes.

Normally the pH value of the culture solution is controlled to be between 8.0 and 8.7.

In the invention, controlling the pH value of the algae culture solution to be between 3.0 and 5.0 is implemented by a method of adding hydrochloric acid or acetic acid or by the addition of water saturated with carbon dioxide.

In the invention, the method of controlling the pH value to be between 8.0 and 8.7 is that sodium bicarbonate is added to control the pH value to be between 8.0 and 8.7.

The invention has the beneficial effects that:

1. An open microalgae culture mode is employed for diatom cultivation, thus realizing economically competitive industrial scale cultivation of diatoms;

2. By controlling the culture solution to be in an acidic environment with relatively low pH value when required, the inhibition of predators once the selected diatom reaches sufficient density continuous production at high density can be maintained.

3. Depending upon the locality and the weather, there is a best choice diatom that will outperform other diatoms in terms of growth. That diatom can be directly obtained from natural seawater or local natural water owing to the open microalgae culture mode, and diatoms in algae culture solutions from different regions and different sea areas differ in specific genus, so different genera of diatoms having local characteristics can be cultivated by the invention, and the algae issues are solved through natural selection of local diatoms without establishing an algae culture base.

DETAILED DESCRIPTION OF THE PREFERRED EMBODIMENTS

In open diatom cultivation, an open microalgae culture device that generally includes a reactor body, a gas absorption system and an alga recovery system is used, the algae culture solution containing diatoms, which can be either fresh water or seawater species, is first introduced into the reactor body of the open microalgae culture system, at this moment, the algae culture solution may contain a variety of unwanted algae and planktons, they will grow together because of their competitive relation in growth, and in the present invention, in order to inhibit growth of the unwanted algae, ensure preferential growth of the target alga, i.e. diatoms, and simultaneously prevent the planktons from ingestion on diatoms, the pH value of the algae culture solution is controlled to be within an acidic range by a method of adding hydrochloric acid or acetic acid or waters saturated with carbon dioxide when required, thus inhibits the growth of these predators.

It is determined in the invention by means of ceaseless tests that: when the pH value of the algae culture solution is about 4, unwanted algae and planktons can be controled satisfactorily by maintaining this pH value for about 30 minutes, at the same time, normal survival of the target algae, i.e. diatoms, is ensured to achieve preferential growth of diatoms. These tests have indicated that, when the pH value is lower than 3.0 or an acidic environment is maintained for more than 120 minutes, inhibition of diatoms will also be generated, and when the pH value is higher than 5.0 or an acidic environment is maintained for less than 30 minutes, other algae and planktons cannot be controlled effectually so as not to ensure preferential growth of the diatoms.

In the invention, excellent diatom cultivation can be reached by such process conditions as controlling the pH value of the algae culture solution to be about 4 and maintaining the pH value for 30-120 minutes, because the diatoms will impose further inhibition on other algae once they attain preference in growth competition, this overcomes a generally-acknowledged technical prejudice in the traditional open microalgae cultivation techniques that a variety of algae will compete and grow together under the same nutrient environment and a single alga cannot be obtained at last, and a brand-new cultivation idea is presented for diatom cultivation.

The pH value will be constantly increased to 9 or above after addition of hydrochloric acid or acetic acid or saturated water solution of carbon dioxide stops because alkaline metabolites are generated in the growth process of diatoms, and a strong alkaline environment is adverse to the growth of diatoms, therefore, the pH value needs to be controlled within a most suitable environment for diatoms. In the invention, the pH value of the cultivation water is controlled and maintained to be between 8.0 and 8.7 by adding sodium bicarbonate, and tests have indicated that this pH value range is most advantageous for the growth of diatoms and can result in best diatom cultivation efficiency.

Finally, it shall be noted that: the aforementioned embodiments are merely for description of the invention, not intended to limit the technical proposal described in the invention; therefore, while the invention has been described in this description in details with reference to a variety of aforementioned embodiments, it shall be understood by those skilled in this art that modifications or equivalent substitutions could still be made to the invention; and any technical proposal without departing from the spirit and scope of the invention as well as the improvements thereof shall be contemplated as being within the claim scope of the invention.

What is claimed is:

1. A method for open diatom cultivation, an open diatom culture device being used, culture solution containing diatoms being introduced to the open culture system, and then carbon dioxide and nutrient salts being added to form a culture solution for diatom cultivation,
   wherein after the algae culture solution containing diatoms is introduced to the open microalgae culture device, the pH value of the algae culture solution is controlled to be between 3.0 and 5.0 and maintained so for 30 to 120 minutes.

2. The method for open diatom cultivation according to claim 1,
   wherein after the algae culture solution containing diatoms is introduced to the open microalgae culture device, the pH value of the algae culture solution is controlled to be between 3.0 and 5.0 and maintained so for 30 to 120 minutes, otherwise the pH value is controlled to be between 8.0 and 8.7.

3. The method for open diatom cultivation according to claim 1,
   wherein controlling the pH value of the algae culture solution to be between 3.0 and 5.0 is implemented by a method of adding hydrochloric acid or acetic acid.

4. The method for open diatom cultivation according to claim 3,
   wherein the method of controlling the pH value to be between 8.0 and 8.7 is that sodium bicarbonate is added to control the pH value to be between 8.0 and 8.7.

5. The method for open diatom cultivation according to claim 2,
   wherein controlling the pH value of the algae culture solution to be between 3.0 and 5.0 is implemented by a method of adding hydrochloric acid or acetic acid.

6. The method for open diatom cultivation according to claim 5,
   wherein the method of controlling the pH value to be between 8.0 and 8.7 is that sodium bicarbonate is added to control the pH value to be between 8.0 and 8.7.

* * * * *